(12) United States Patent
Govari et al.

(10) Patent No.: US 11,432,872 B2
(45) Date of Patent: Sep. 6, 2022

(54) ENERGY-GUIDED RADIOFREQUENCY (RF) ABLATION

(71) Applicant: BIOSENSE WEBSTER (ISRAEL) LTD., Yokneam (IL)

(72) Inventors: Assaf Govari, Haifa (IL); Andres Claudio Altmann, Haifa (IL); Ella Ozeri, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 448 days.

(21) Appl. No.: 16/288,838

(22) Filed: Feb. 28, 2019

(65) Prior Publication Data
US 2020/0275971 A1 Sep. 3, 2020

(51) Int. Cl.
A61B 18/12 (2006.01)
A61B 18/14 (2006.01)
A61B 18/00 (2006.01)

(52) U.S. Cl.
CPC ...... *A61B 18/1492* (2013.01); *A61B 18/1206* (2013.01); *A61B 2018/00351* (2013.01); *A61B 2018/00577* (2013.01); *A61B 2018/00702* (2013.01); *A61B 2018/00744* (2013.01); *A61B 2018/00791* (2013.01); *A61B 2218/002* (2013.01)

(58) Field of Classification Search
CPC ............ A61B 18/1492; A61B 18/1206; A61B 2018/00351; A61B 2018/00577; A61B 2018/00702; A61B 2018/00744; A61B 2018/00791; A61B 2218/002; A61B 2018/00029; A61B 2018/00357; A61B 2018/00886; A61B 2018/00875; A61B 2018/00011; A61B 2018/00678; A61B 18/12; A61B 2018/00648

USPC .......................................................... 606/41
See application file for complete search history.

(56) References Cited

U.S. PATENT DOCUMENTS

| 9,717,552 | B2* | 8/2017 | Cosman ............ A61B 18/1482 |
| 2004/0158237 | A1 | 8/2004 | Abboud et al. |
| 2005/0096712 | A1* | 5/2005 | Abraham-Fuchs ........................ A61B 1/00158 607/89 |
| 2005/0101946 | A1* | 5/2005 | Govari .................. A61B 18/14 606/33 |
| 2005/0256522 | A1* | 11/2005 | Francischelli ..... A61B 18/1442 606/41 |
| 2007/0173813 | A1* | 7/2007 | Odom ................ A61B 18/1445 606/51 |

(Continued)

FOREIGN PATENT DOCUMENTS

| EP | 2942023 A2 | 11/2015 |
| EP | 3375396 A1 | 9/2018 |

OTHER PUBLICATIONS

European Search Report for corresponding EPA No. 20159839.8 dated Jul. 12, 2020.

*Primary Examiner* — Daniel W Fowler
(74) *Attorney, Agent, or Firm* — Dergosits & Noah LLP; Todd A. Noah

(57) ABSTRACT

A method of body tissue ablation includes defining a target amount of ablation energy needed to create a specified lesion in tissue in a body of a patient. Contact is made between an ablation probe and the tissue. Using the ablation probe, an ablation signal is applied to the tissue, which delivers the target amount of ablation energy during a smallest time duration permitted within a defined maximum-power constraint.

19 Claims, 2 Drawing Sheets

(56) References Cited

U.S. PATENT DOCUMENTS

| | | | |
|---|---|---|---|
| 2010/0211070 A1* | 8/2010 | Subramaniam | A61B 18/1206 606/49 |
| 2012/0157890 A1 | 6/2012 | Govari et al. | |
| 2013/0178738 A1* | 7/2013 | Martin | A61B 8/12 600/439 |
| 2013/0317363 A1* | 11/2013 | Case | A61B 8/4263 600/439 |
| 2014/0128881 A1* | 5/2014 | Tyc | A61B 18/06 606/130 |
| 2017/0209208 A1 | 7/2017 | Govari et al. | |
| 2018/0263689 A1* | 9/2018 | Govari | A61B 18/1492 |

* cited by examiner

ENERGY-GUIDED RADIOFREQUENCY (RF) ABLATION

FIELD OF THE INVENTION

The present invention relates generally to radiofrequency (RF) ablation, and particularly to cardiac RF ablation.

BACKGROUND OF THE INVENTION

Techniques for controlling RF ablation were previously proposed in patent literature. For example, U.S. Patent Application Publication 2004/0158237 describes an integrated multiple energy ablation system that allows for a variety of ablation procedures to be performed without the interchanging of catheters. A console is provided that is connected to one or more energy treatment devices such as catheters or probes, via an energy-delivering umbilical system. The integrated ablation station is designed to be compatible with commercial catheters and allows for sequential or simultaneous ablation and mapping procedures to be performed when a deeper and wider lesion capability and/or a broader temperature ablation spectrum is desired. Incorporating a closed system of fluid circulation allows circulating fluid to cool an RF catheter ablation electrode during delivery of radiofrequency energy.

As another example, U.S. Patent Application Publication 2017/0209208 describes a method, including selecting a first maximum radiofrequency (RF) power to be delivered by an electrode within a range of 70 W-100 W, and selecting a second maximum RF power to be delivered by the electrode within a range of 20 W-60 W. The method also includes selecting an allowable force on the electrode within a range of 5 g-50 g, selecting a maximum allowable temperature, of tissue to be ablated, within a range of 55-65° C., and selecting an irrigation rate for providing irrigation fluid to the electrode within a range of 8-45 ml/min. The method further includes performing an ablation of tissue using the selected values by initially using the first power, switching to the second power after a predefined time between 3 s and 6 s, and terminating the ablation after a total time for the ablation between 10 s and 20 s.

U.S. Patent Application Publication 2012/0157890 describes body tissue ablation that is carried out by inserting a probe into a body of a living subject, urging the probe into contact with a tissue in the body, generating energy at a power output level, and transmitting the generated energy into the tissue via the probe. While transmitting the generated energy the ablation is further carried out by determining a measured temperature of the tissue and a measured power level of the transmitted energy, and controlling the power output level responsively to a function of the measured temperature and the measured power level. Related apparatus for carrying out the ablation is also described.

SUMMARY OF THE INVENTION

An embodiment of the present invention provides a method of body tissue ablation, including defining a target amount of ablation energy needed to create a specified lesion in tissue in a body of a patient. Contact is made between an ablation probe and the tissue. Using the ablation probe, an ablation signal is applied to the tissue, which delivers the target amount of ablation energy during a smallest time duration permitted within a defined maximum-power constraint.

In some embodiments, the method further includes, during application of the ablation signal, applying irrigation fluid in a vicinity of the tissue. A temperature is monitored in the vicinity of the tissue, and if the monitored temperature exceeds a defined maximum-temperature limit, a flow of the irrigation fluid is increased.

In some embodiments, the method further includes, if the monitored temperature exceeds the defined maximum-temperature limit but the flow of the irrigation fluid exceeds a defined maximum-flow limit, reducing a power of the ablation signal and extending the time duration of the ablation signal.

In an embodiment, monitoring the temperature includes measuring the temperature of an electrode that delivers the ablation signal to the tissue. In another embodiment, the method further includes extending a duration of ablation until the preset amount of ablation energy to be applied to the tissue is reached.

In some embodiments, the method further includes, during application of the ablation signal, applying irrigation fluid in a vicinity of the tissue. A temperature is monitored in the vicinity of the tissue, and if the monitored temperature exceeds a defined maximum-temperature limit, a power of the ablation signal is decreased to keep the temperature at the maximum-temperature limit up to a given tolerance.

In some embodiments, the method further includes, during application of the ablation signal, if power of the ablation signal is decreasing, increasing an irrigation flow to reduce the temperature below the maximum-temperature limit and subsequently increasing the power of the ablation signal to the maximum-power target.

In an embodiment, the method further includes, during application of the ablation signal, if the target amount of ablation energy is not met during the time duration permitted, stopping the ablation signal.

There is additionally provided, in accordance with an embodiment of the present invention, a system for body tissue ablation, the system including a memory, an ablation probe, a generator, and a processor. The memory is configured to store a value of target amount of ablation energy needed to create a specified lesion in tissue in a body of a patient. The ablation probe is configured to make contact with tissue. The generator is configured to generate an ablation signal. The processor is configured to control the generator and the ablation probe to apply the ablation signal to the tissue with the target amount of ablation energy during a smallest time duration permitted within a defined maximum-power constraint.

The present invention will be more fully understood from the following detailed description of the embodiments thereof, taken together with the drawings in which:

DETAILED DESCRIPTION OF EMBODIMENTS

Overview

Figure 1:
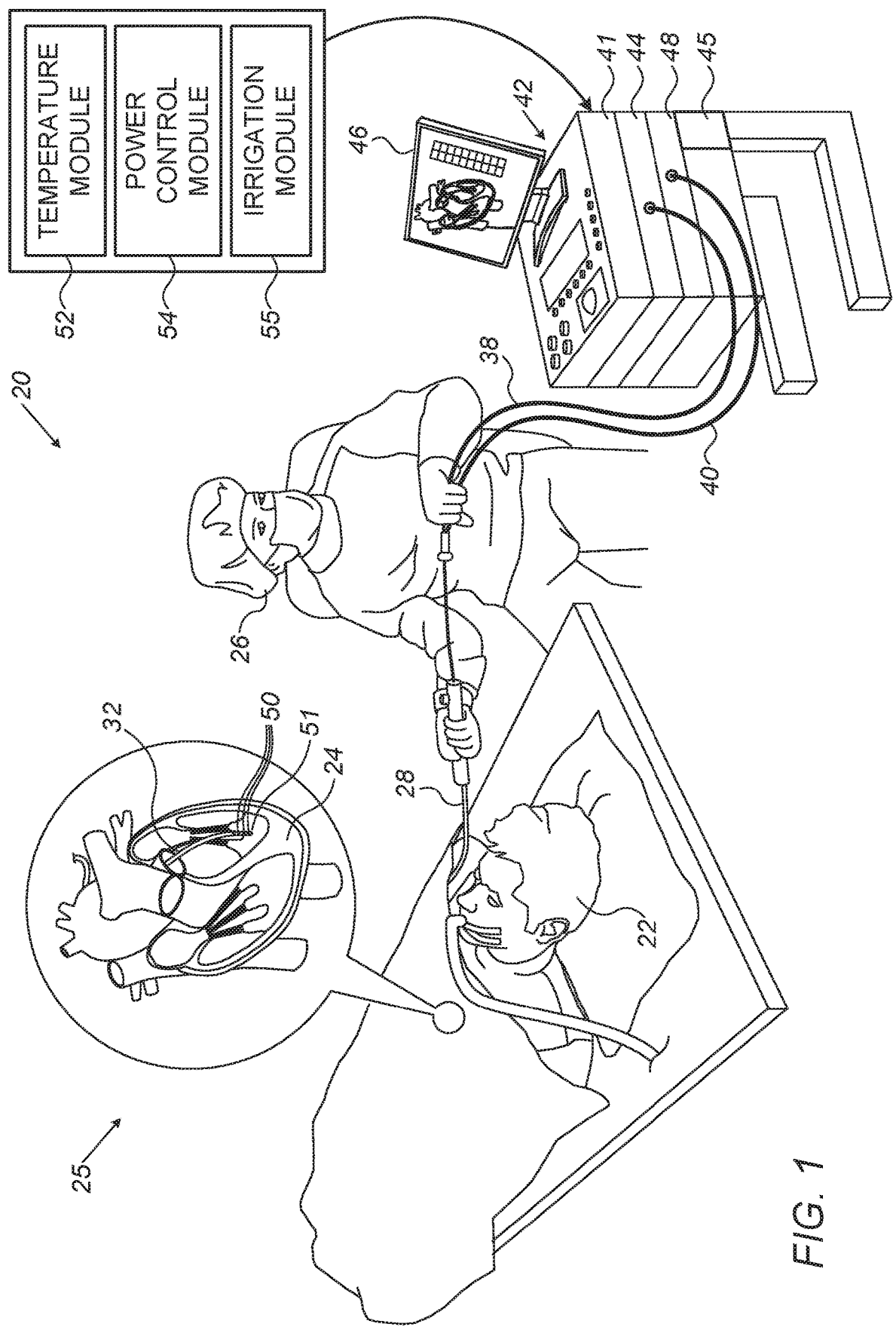
FIG. 1 is a schematic, pictorial illustration of a system for cardiac radiofrequency (RF) ablation therapy, in accordance with an embodiment of the present invention.

Cardiac radiofrequency (RF) ablation systems may vary the amount of ablative energy and a corresponding lesion depth. To accomplish this, such systems may vary both the irrigation rate and the RF power input, as well as the duration of ablation, while ensuring that the temperature of the ablated tissue does not exceed a maximum value. However, during the ablation, for example with thin tissues, the tissue may sometimes a poor temperature response (e.g., the temperature may rise/fall unexpectedly). The amount of energy, which varies correspondingly, may cause uncontrolled lesion depth.

Embodiments of the present invention that are described hereinafter operate an ablation system in a constant energy mode, wherein, within constraints, a preset amount of ablating RF energy is applied to tissue within the shortest possible time to achieve a preplanned lesion depth. (The short ablation time assists in concentrating the energy in the desired lesion area, i.e., reduces the amount of energy that escapes the desired area.) A maximal RF power level is set, yielding a nominal time for ablation. During the ablation the temperature is monitored to maintain temperature within an allowable temperature range comprising high and low temperature limits.

During the ablation the irrigation flow rate and the power output level are adjusted to maintain maximal possible RF power, while keeping the temperature within its allowed range. In some embodiments, when the applied RF power level is lowered, ablation time is extended so that the preset amount of ablating RF energy target is met.

Typically, a processor running an algorithm for the ablation commands an increased irrigation flow rate within the allowable flow rate range, so that the ablation power can be maintained at the highest possible level allowed by the preset upper power limit and temperature range. In other words, lowering power is reverted to only as a last resort, when it is impossible to stay below the maximum temperature limit using irrigation alone.

In some embodiments, the disclosed method includes the steps of (a) defining a target amount of ablation energy needed to create a specified lesion in tissue in a body of a patient, (b) making contact between an ablation probe and the tissue, and (c) using the ablation probe, applying to the tissue an ablation signal, which delivers the target amount of ablation energy during a smallest time duration permitted within a defined maximum-power constraint.

In some embodiments, during application of the ablation signal, the disclosed method further includes applying irrigation fluid in a vicinity of the tissue and monitoring a temperature in the vicinity of the tissue. If the monitored temperature exceeds a defined maximum-temperature limit, the processor commands increasing a flow of the irrigation fluid.

If the monitored temperature exceeds the defined maximum-temperature limit but the flow of the irrigation fluid exceeds a defined maximum-flow limit, the processor commands reducing a power of the ablation signal and extending the time duration of the ablation signal.

The disclosed RF ablation technique, according to a target amount of RF energy to be disposed in tissue, allows maintaining maximal RF power level for a shorter duration and thus may improve the clinical outcome of a catheter-based RF ablation procedure.

System Description

FIG. 1 is a schematic, pictorial illustration of a system 12 for cardiac radiofrequency (RF) ablation therapy, in accordance with an embodiment of the present invention. Typically, a memory 45 of system 20 stores numerous ablation protocols for different clinical scenarios, such as the protocol described in FIG. 2.

A physician 26 inserts a catheter 28 through a blood vessel into a chamber of a heart 24 of a subject 22, and manipulates the catheter so that a distal end 32 of the catheter contacts the endocardium in an area that is to be treated. A tip electrode 51 of catheter 28, seen in inset 25, comprises one or more temperature sensors 50, which measure the temperature of the electrode. In some embodiments this temperature is used as an estimate of the temperature in the vicinity of the ablated tissue.

After positioning distal end 32 at an ablation site, and ensuring that the tip is in contact with the endocardium, operator 26 actuates an RF energy generator 44 in a control console 42 to supply RF energy via a cable 38 to distal end 32. Meanwhile, an irrigation pump 48 supplies a cooling fluid, such as normal saline solution, via a tube 40 and a lumen in catheter 28 to the distal end. Typically, both before and during the ablation, a display 46 displays values of the ablation parameters, such as those listed in Tables I-IV below, to physician 26.

Operation of the RF energy generator and the irrigation pump may be coordinated in order to give the appropriate volume of irrigation during ablation, so as to cool the tip of the catheter and the tissue without overloading the heart with irrigation fluid. Each temperature sensor inside temperature sensors 50 provides feedback to console 42 for use, for example, in controlling the RF energy dosage and/or irrigation volume.

In order to operate system 12, a processor 41 includes a number of modules used by the processor to operate the system. These modules comprise a temperature module 52, a power control module 54, and an irrigation module 55, the functions of which are described below. In particular, processor 41 runs a dedicated algorithm as disclosed herein, included in FIG. 2, that enables processor 41 to perform the disclosed steps, as further described below.

Although the pictured embodiment relates specifically to the use of a tip ablation device for ablation of heart tissue, the methods described herein may alternatively be applied in ablation devices comprising multiple ablation electrodes when the operation of each electrode is independently controlled by processor 41.

Energy-Guided RF Ablation

Figure 2:
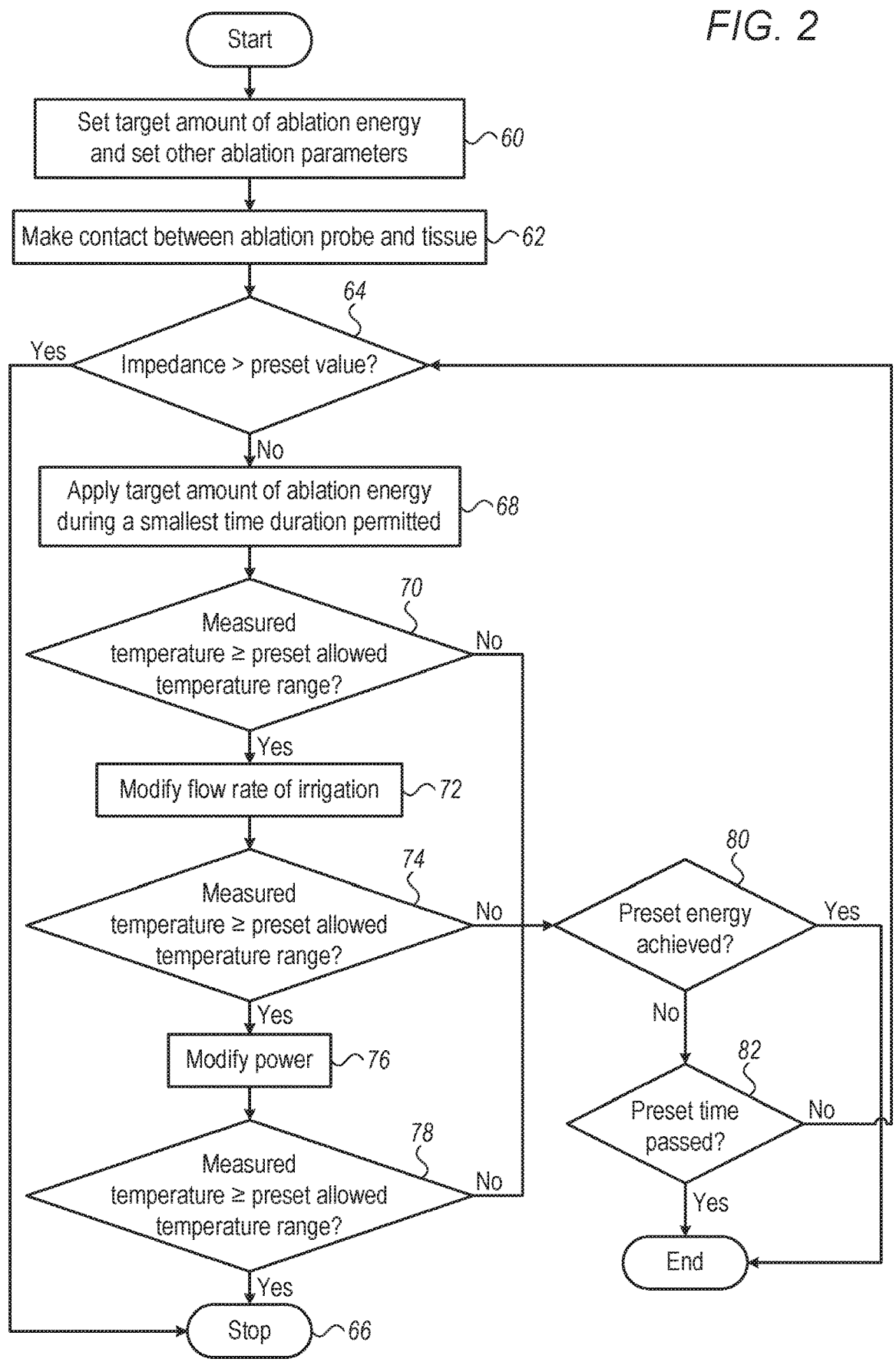
FIG. 2 is a flow chart that schematically illustrates steps of an algorithm performed in operation of the RF ablation system of FIG. 1, according to an embodiment of the present invention.

FIG. 2 is a flow chart that schematically illustrates steps of an algorithm performed in operation of RF ablation system 20 of FIG. 1, according to an embodiment of the present invention. The process begins at an ablation parameter presetting step 60, in which physician 26 presets each of the variable ablation parameters referred to above, and in particular sets target amount of ablation energy. Such a step may involve generating many protocols for different clinical scenarios, where such protocols are saved, for example, in memory 45 of system 20.

In some embodiments, the ablation parameters are set as shown in one of Tables I-IV. Typically, for the RF power, an operator of the system only sets the maximal RF power, while the minimal RF power is automatically set by the system to zero for safety reasons.

Tables I-IV provide four different settings that may be used for optimizing lesion depth while minimizing collateral damage, depending on the clinical need for example:

Table I— Low depth (less than 2 mm)
Table II— Medium depth (2 mm-3.5 mm)

Table III— High depth (3.5 mm-5.0 mm)
Table IV— Extra depth (more than 5.0 mm)
Low Depth Parameters:

TABLE I

| Parameter | Range |
|---|---|
| Preset ablative energy | 270 J |
| Maximum power level | 90 W |
| Power range | 0-90 W |
| Allowable temperature range | 45-65° C. (typically 50° C.) |
| Allowable irrigation flow rate | 4-25 ml/min (this is mainly depending on the catheter design. (Typically, 4-15 ml/min) |
| Maximal ablation time | 3-6 Sec (Typically 4 sec) |

Medium Depth Parameters:

TABLE II

| Parameter | Range |
|---|---|
| Preset ablative energy | 360 J |
| Maximum power level | 90 W |
| Power range | 0-90 W |
| Allowable temperature range | 45-65° C. (typically 50° C.) |
| Allowable irrigation flow rate | 4-25 ml/min (mainly depending on the catheter design. (Typically, 4-15 ml/min) |
| Maximal ablation time | 4-8 Sec (Typically 6 sec) |

High Depth Parameters:

TABLE III

| Parameter | Range |
|---|---|
| Preset ablative energy | 560 J |
| Maximum power level | 70-90 W (Typically 70 W) |
| Power range | 0-90 W |
| Allowable temperature range | 45-65° C. (typically 50° C.) |
| Allowable irrigation flow rate | 4-25 ml/min (mainly depending on the catheter design. (Typically, 4-15 ml/min) |
| Maximal ablation time | 6-12 Sec (Typically 10 sec) |

Extra High Depth Parameters:

TABLE IV

| Parameter | Range |
|---|---|
| Preset ablative energy | 1500-3000 J |
| Maximum power level | 50 W |
| Power range | 0-50 W |
| Allowable temperature range | 40-55° C. (typically 45° C.) |
| Allowable irrigation flow rate | 4-25 ml/min (mainly depending on the catheter design. Typically, 4-15 ml/min) |
| Maximal ablation time | 30-90 Sec (Typically 60 sec) |

Ablation parameter setting step 60 is implemented before physician 26 performs an ablation.

At the beginning of an ablation session, in a probe introduction step 62, physician 26 inserts catheter 28 into a desired location in heart 24, using a catheter position tracking system incorporated into system 20. At that step, physician 26 brings catheter 28 into contact with target cardiac tissue.

At an impedance decision step 64, processor 41 uses power control module 54 to check if the impedance of electrode 51 is more than a preset impedance value. If it is, the system halts the ablation procedure for electrode 51 in a termination step 66. If step 64 returns a negative value, control of the algorithm continues to RF ablation step 68.

At RF delivery step 68, physician 26 operates system 20, with a particular ablation protocol the physician selected, for which the parameter values were selected in step 60. Physician 26 task is to perform the preset ablation protocol by applying (e.g., with electrode 51) the target amount of energy during a smallest time duration permitted, as, for example, shown in table I. Display 46 of system 20 may be configured to display to the physician 26, by methods which are known in the art, the progress of the RF delivery to the electrode. The display of the progress may be graphical, such as a simulation of the dimensions of a respective lesion as it is produced by the ablation, and/or by way of an alphanumeric display.

During the RF delivery procedure, processor 41 uses temperature module 52 to perform a number of checks on the progress of the procedure, as shown in the flow chart by decision steps 70, 74, and 78. Irrigation module 55 and power control module 54 perform modifications, as shown in the flowchart, by modification steps 72 and 76.

In alternative embodiments, temperature is checked, and if the temperature reaches a prespecified target, the processor instructs the generator to decrease power to keep the temperature in the range of the prespecified temperature target. If the system identifies that power is decreased by more than a given power (for example by 1 W) the irrigation flow is increased to prevent the power from decreasing. Increasing the flow enables increasing the power while keeping the temperature on target.

At a first temperature decision step 70, the processor uses temperature module 52 to check if the measured tissue temperature deviated from the allowable preset temperature range selected in step 60. If temperature decision step 70 returns a positive answer, irrigation control module 55 modifies the flow rate of irrigation to bring temperature into the allowable range, at an irrigation modification step 72.

At a second temperature decision step 74, the processor uses temperature module 52 to recheck if the measured tissue temperature deviated from the allowable preset temperature range selected in step 60. If temperature decision step 74 returns a positive answer, power control module 54 modifies the power to electrode 51 to bring temperature into the allowable range, at a power modification step 76.

If modifications of steps 72 and 76 were unsuccessful in controlling tissue temperature according to Table I, the system halts the ablation procedure for the electrode 51 at a termination step 66.

If any of decision steps 70, 74, or 78 returns a negative answer, control continues to ablation decision step 80.

At ablation decision step 80, processor 41 checks if the amount of ablative energy deposited by the given electrode, set in step 60, has been reached. If it has, then the process ends. If the energy has not been reached or was exceeded, control passes to a duration decision step 82, in which processor 41 checks if the maximal time of ablation, set in step 60, has been reached or exceeded. If the maximal preset time has been reached the system halts the procedure for the electrode 51 in termination step 66. Otherwise the process loops back to decision step 64.

Decision steps 64, 70, 74, 78, 80, and 82 have been presented sequentially in the flowchart for simplicity and clarity. Typically, however, the system uses the power control module to perform these steps in parallel.

The example flow chart shown in FIG. 2 is chosen purely for the sake of conceptual clarity. The present embodiment also comprises additional steps of the algorithm, such as checking a level of contact force of electrode 51 with tissue, which have been omitted from the disclosure herein purposely on order to provide a more simplified flow chart.

In an embodiment, the disclosed method further includes, during application of the ablation signal, the steps of applying irrigation fluid in a vicinity of the tissue, monitoring a temperature in the vicinity of the tissue, and if the monitored temperature exceeds a defined maximum-temperature limit, decreasing a power of the ablation signal to keep the temperature at the maximum-temperature limit up to a given tolerance.

In another embodiment, the disclosed method further includes, during application of the ablation signal, the step of, if the power of the ablation signal is decreasing, increasing an irrigation flow to reduce the temperature below the maximum-temperature limit and subsequently increasing a power of the ablation signal to the maximum-power target.

In yet another embodiment, the disclosed method further includes, during application of the ablation signal, if the target amount of ablation energy is not met during the time duration permitted, stopping the ablation signal.

Although the embodiments described herein mainly address cardiac applications, the methods and systems described herein can also be used, for example, in ablating other organs of the body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of body tissue ablation, the method comprising:
   a) setting ablation parameters needed to create a specified lesion in tissue in a body of a patient using an ablation probe having an electrode, the ablation parameters comprising a target amount of ablation energy, a predetermined temperature range of the tissue, a range of power to be delivered to the electrode, the range including a maximum power level, and a preset period of time;
   b) determining that an impedance of the electrode does not exceed a preset impedance value;
   c) applying an ablation signal to the tissue to deliver the target amount of ablation energy during a smallest time duration within the preset period of time using the maximum power level;
   d) modifying an irrigation flow rate in response to a determination that a monitored tissue temperature equals or exceeds a maximum temperature within the preset temperature range;
   e) modifying the power in response to a determination that the monitored tissue temperature equals or exceeds the maximum temperature after modifying the irrigation flow rate;
   f) discontinuing the ablation signal in response to one of:
      i) a determination that the monitored tissue temperature equals or exceeds the maximum temperature after modifying the irrigation flow rate and power,
      ii) a determination that the monitored tissue temperature does not equal or exceed the maximum temperature after one of modifying the irrigation flow rate or power and a determination that the target amount of ablation energy has been achieved, or
      iii) a determination that the monitored tissue temperature does not equal or exceed the maximum temperature after one of modifying the irrigation flow rate or power, a determination that the target amount of ablation energy has not been achieved and a determination that the preset period of time has been exceeded; and
   g) returning to step b) if the ablation is not discontinued pursuant to step f).

2. The method according to claim 1, and comprising, if the monitored temperature exceeds the defined maximum temperature but the flow of the irrigation fluid exceeds a defined maximum-flow limit, reducing the power and extending the time duration of the ablation signal.

3. The method according to claim 1, wherein monitoring the temperature comprises measuring the temperature of the electrode that delivers the ablation signal to the tissue.

4. The method according to claim 1, and comprising extending a duration of ablation until the target amount of ablation energy to be applied to the tissue is reached.

5. The method according to claim 1, and comprising, during application of the ablation signal:
   applying irrigation fluid in a vicinity of the tissue;
   monitoring a temperature in the vicinity of the tissue; and
   if the monitored temperature exceeds the maximum temperature, decreasing the power to keep the temperature at the maximum temperature.

6. The method according to claim 5, and comprising, during application of the ablation signal, if the power is decreasing, increasing the irrigation flow to reduce the temperature below the maximum temperature and subsequently increasing the power to the maximum power level.

7. The method according to claim 1, and comprising, during application of the ablation signal, if the target amount of ablation energy is not met during the preset period of time, discontinuing the ablation signal.

8. A system comprising:
   one or more processors; and
   a non-transitory computer readable medium storing a plurality of instructions, which when executed, cause the one or more processors to:
   a) set ablation parameters needed to create a specified lesion in tissue in a body of a patient using an ablation probe having an electrode, the ablation parameters comprising a target amount of ablation energy, a predetermined temperature range of the tissue, a range of power to be delivered to the electrode, the range including a maximum power level, and a preset period of time;
   b) determine that an impedance of the electrode does not exceed a preset impedance value;
   c) apply an ablation signal to the tissue to deliver the target amount of ablation energy during a smallest time duration within the preset period of time using the maximum power level;

d) modify an irrigation flow rate in response to a determination that a measured tissue temperature equals or exceeds a maximum temperature within the preset temperature range;
e) modify the power in response to a determination that the measured tissue temperature equals or exceeds the maximum temperature after modifying the irrigation flow rate;
f) discontinue the ablation signal in response to one of:
  i) a determination that the measured tissue temperature equals or exceeds the maximum temperature after modifying the irrigation flow rate and power,
  ii) a determination that the measured tissue temperature does not equal or exceed the maximum temperature after one of modifying the irrigation flow rate or power and a determination that the target amount of ablation energy has been achieved, or
  iii) a determination that the measured tissue temperature does not equal or exceed the maximum temperature after one of modifying the irrigation flow rate or power, a determination that the target amount of ablation energy has not been achieved and a determination that the preset period of time has been exceeded; and
g) return to step b) if the ablation is not discontinued pursuant to step f).

9. The system according to claim 8, wherein, if the monitored temperature exceeds the defined maximum temperature but the flow of the irrigation fluid exceeds a defined maximum-flow limit, the plurality of instructions, when executed, will further cause the one or more processors to reduce the power and extend the time duration of the ablation signal.

10. The system according to claim 8, wherein the monitored temperature is the temperature of the electrode that delivers the ablation signal to the tissue.

11. The system according to claim 8, wherein the plurality of instructions, when executed, will further cause the one or more processors to control the generator to extend a duration of ablation until the target amount of ablation energy to be applied to the tissue is reached.

12. The system according to claim 8, wherein the plurality of instructions, when executed, will further cause the one or more processors to, during application of the ablation signal:
  apply irrigation fluid in a vicinity of the tissue;
  monitor a temperature in the vicinity of the tissue; and
  if the monitored temperature exceeds the maximum temperature, decreasing the power to keep the temperature at the maximum temperature.

13. The system according to claim 12, wherein the plurality of instructions, when executed, will further cause the one or more processors to, during application of the ablation signal, if the power is decreasing, increasing the irrigation flow to reduce the temperature below the maximum temperature and subsequently increasing the power to the maximum power level.

14. A computer program product, comprising a non-transitory computer-readable medium having computer-readable program code embodied therein to be executed by one or more processors, the program code including instructions to:
a) set ablation parameters needed to create a specified lesion in tissue in a body of a patient using an ablation probe having an electrode, the ablation parameters comprising a target amount of ablation energy, a predetermined temperature range of the tissue, a range of power to be delivered to the electrode, the range including a maximum power level, and a preset period of time;
b) determine that an impedance of the electrode does not exceed a preset impedance value;
c) apply an ablation signal to the tissue to deliver the target amount of ablation energy during a smallest time duration within the preset period of time using the maximum power level;
d) modify an irrigation flow rate in response to a determination that a measured tissue temperature equals or exceeds a maximum temperature within the preset temperature range;
e) modify the power in response to a determination that the measured tissue temperature equals or exceeds the maximum temperature after modifying the irrigation flow rate;
f) discontinue the ablation signal in response to one of:
  i) a determination that the measured tissue temperature equals or exceeds the maximum temperature after modifying the irrigation flow rate and power,
  ii) a determination that the measured tissue temperature does not equal or exceed the maximum temperature after one of modifying the irrigation flow rate or power and a determination that the target amount of ablation energy has been achieved, or
  iii) a determination that the measured tissue temperature does not equal or exceed the maximum temperature after one of modifying the irrigation flow rate or power, a determination that the target amount of ablation energy has not been achieved and a determination that the preset period of time has been exceeded; and
g) return to step b) if the ablation is not discontinued pursuant to step f).

15. The computer program product according to claim 14, wherein the program code includes further instructions to reduce the power and extend the time duration of the ablation signal if the monitored temperature exceeds the defined maximum temperature and the flow of the irrigation fluid exceeds a defined maximum-flow limit.

16. The computer program product according to claim 14, wherein the monitored temperature is the temperature of the electrode that delivers the ablation signal to the tissue.

17. The computer program product according to claim 14, wherein the program code includes further instructions to control the generator to extend a duration of ablation until the target amount of ablation energy to be applied to the tissue is reached.

18. The computer program product according to claim 14, wherein the program code includes further instructions to, during application of the ablation signal:
  apply irrigation fluid in a vicinity of the tissue;
  monitor a temperature in the vicinity of the tissue; and
  if the monitored temperature exceeds the maximum temperature, decreasing the power to keep the temperature at the maximum temperature.

19. The computer program product according to claim 18, wherein the plurality of instructions, when executed, will further cause the one or more processors to, during application of the ablation signal, if the power is decreasing, increasing the irrigation flow to reduce the temperature below the maximum temperature and subsequently increasing the power to the maximum power level.

* * * * *